United States Patent [19]
de Salvert

[11] Patent Number: 5,827,520
[45] Date of Patent: Oct. 27, 1998

[54] VEHICLE AND COMPOSITION CONTAINING THIS VEHICLE AND A STABILIZED COSMETIC OR DERMATOLOGICAL ACTIVE SUBSTANCE

[75] Inventor: Armelle de Salvert, Paris, France

[73] Assignee: L'Oreal, Paris, France

[21] Appl. No.: 734,779

[22] Filed: Oct. 22, 1996

[30] Foreign Application Priority Data

Oct. 23, 1995 [FR] France ................................. 95 12446

[51] Int. Cl.$^6$ ..................................................... A61K 7/43
[52] U.S. Cl. .............................. 424/401; 424/59; 424/63; 424/70.11; 424/70.12
[58] Field of Search ............... 424/401, 59, 63, 424/70.11, 70.12

[56] References Cited

U.S. PATENT DOCUMENTS 4,673,569   6/1987   Shernov et al. .
5,540,853   7/1996   Trinh ........................................ 510/101

FOREIGN PATENT DOCUMENTS

| 0 404 532 | 12/1990 | European Pat. Off. . |
| 0 437 956 | 7/1991 | European Pat. Off. . |
| 0 623 338 | 11/1994 | European Pat. Off. . |
| 487404 | 5/1995 | European Pat. Off. . |
| 61-207499 | 9/1986 | Japan . |
| 61-254244 | 11/1986 | Japan . |
| 63-130514 | 6/1988 | Japan . |

*Primary Examiner*—Thurman K. Page
*Assistant Examiner*—D. Faulkner
*Attorney, Agent, or Firm*—Oblon, Spivak, McClelland, Maier & Neustadt, P.C.

[57] ABSTRACT

A stabilized cosmetic or dermatological active composition containing a vehicle comprising not more than 10% by weight of water, at least one amphiphilic oil, at least one polyol or polyol derivative selected from the group consisting of $C_2$–$C_4$ glycols, ether derivatives of a $C_2$–$C_4$ glycol and mixtures thereof, and at least one solvent for oil and water, containing an alcohol functional group.

26 Claims, No Drawings

VEHICLE AND COMPOSITION CONTAINING THIS VEHICLE AND A STABILIZED COSMETIC OR DERMATOLOGICAL ACTIVE SUBSTANCE

This application is a continuation of PCT 95/12446 France published 27 Aug. 1996.

FILED OF THE INVENTION

The present invention relates to a vehicle including not more than 10% by weight of water, at least one amphiphilic oil, at least one polyol or polyol derivative chosen from $C_2$–$C_4$ glycols and ether derivatives of a $C_2$–$C_4$ glycol and at least one common solvent for water and oil, chosen from primary alcohols and $C_5$–$C_7$ glycols. This vehicle forms a transparent or translucent fluid which is homogeneous and stable although it contains no surfactant or stabilizer.

The vehicle according to the invention can be employed especially in a composition for topical action containing active substances which are sensitive to external factors and/or to water, such as dihydroxyacetone, vitamin C or enzymes. These active substances remain stable in such a vehicle.

The composition obtained can be employed especially for the cosmetic and/or dermatological treatment of the skin, including the scalp.

The present invention relates to a vehicle forming a medium which is stable although free from surfactant and stabilizer, and capable of being employed in a composition containing an active substance that is sensitive to external factors and/or to water, and to the use of such a composition for the cosmetic and/or dermatological treatment of the skin, including the scalp.

DESCRIPTION OF THE BACKGROUND

It is known to introduce active substances into cosmetic and/or dermatological compositions to provide treatments which are specific to the skin, for example for combating the dryness, aging or pigmentation of the skin, for treating acne or certain skin diseases (eczema, psoriasis), for fighting against excess weight, for promoting the restructuring of the skin or its cell renewal, and for coloring the skin.

Ascorbic acid (or vitamin C), for example, is known to stimulate the growth of connective tissue such as collagen. It also makes it possible to strengthen the defenses of the cutaneous tissue against external attacks such as ultraviolet radiation or pollution. It is also employed for removing skin marks and pigmentation, and for promoting cicatrization of the skin.

It is also known that the application of retinol or vitamin A makes it possible to fight in particular against skin aging and against some skin disorders such as acne or keratinization or cicatrization complaints.

Furthermore, the prior art has for many years taught the involvement of dihydroxyacetone in artificial skin coloring (Bobin et al., J. Soc. Cosmet. Chem., 35, pages 265–272, 1984). Dihydroxyacetone reacts with the amino acids naturally present in the lipid film of the stratum corneum and forms melanoids by a Maillard reaction (L. C. Maillard, C. R. Acad. Sci., 154, 66–68, 1912). The application of dihydroxyacetone to the skin therefore makes it possible to give the latter the appearance of a suntanned skin without having the disadvantages (burns, risks of cancer) encountered on exposure to the sun.

In addition, it is also known to introduce enzymes into cosmetic compositions, and especially proteases and lipases employed because of their proteolytic and lipolytic properties. These enzymes are sought after in the field of cosmetics because of their smoothing and cleansing power and their ability to remove the dead cells from the skin.

Unfortunately, some active substances, and in particular those referred to above, are unstable because of their sensitivity to external factors such as light, heat or the presence of oxygen either in air or present in water. The stability of dihydroxyacetone, of vitamin C, of vitamin A or of enzymes in a composition is thus quite relative: in a composition these active substances degrade in the course of time.

This instability runs counter to the effectiveness which is sought and can, furthermore, be a source of unpleasantness for the user; for example, the instability of the active substance may lead to color and/or odor changes in the composition containing it.

Accordingly, various means have been envisaged for stabilizing these active substances. When the active substance comprises a reactive site, especially in the case of vitamins and of dihydroxyacetone, one of the means for stabilizing it consists, for example, in blocking this site by esterification, especially with phosphated, sulphated or alkylated derivatives and in employing these derivatives instead of the free active substance. Unfortunately, the activity exhibited by these derivatives is less good than that of the free active substance.

It has also been envisaged to employ precursors of such active substances, which, after application to the skin, are broken down by the skin enzymes and then release the free active substance (see EP-A-487404). However, the use of such derivatives does not always permit a release of active substance which is rapid and in sufficient quantity at the skin surface.

In addition, it has been envisaged to put an active substance, especially an enzyme, in a pulverulent composition (see JP-A-63-130514). It has also been envisaged to employ these active substances, and especially enzymes, in an immobilized form on polymeric bases (see JP-A-61-207499) or in microcapsules (see JP-A-61-254244). Unfortunately, these means require special processing, and this increases the cost and the time of preparation of the composition.

When the active substances are water-sensitive, another solution consists in incorporating them into an anhydrous liquid medium (see U.S. Pat. No. 5,322,683). Unfortunately, this solution limits the galenic form of the composition and does not permit the incorporation of hydrophilic active substances.

A need therefore continues to exist for a composition in which sensitive cosmetic and/or dermatological active substances would retain all their properties and therefore their effectiveness in the course of time.

SUMMARY OF THE INVENTION

A vehicle which comprises not more than 10% by weight of water, at least one amphiphilic oil, at least one polyol or polyol derivative selected from the group consisting of $C_2$–$C_4$ glycols, ether derivatives of a $C_2$–$C_4$ glycol and mixtures thereof, and at least one solvent for oil and water, containing an alcohol functional group.

The applicant has now found unexpectedly that a vehicle including not more than 10% by weight of water, an amphiphilic oil, a $C_2$–$C_4$ glycol or an ether derivative of a $C_2$–$C_4$ glycol, mixed with a primary alcohol and/or a $C_5$–$C_7$ glycol is capable of maintaining the activity of an active substance which is sensitive to the external factors and/or to water and of preventing the degradation of this active substance.

DETAILED DESCRIPTION OF THE PREFERRED EMBODIMENTS

The present invention provides a vehicle that includes
not more than 10% by weight of water,
at least one amphiphilic oil, at least one polyol or polyol derivative chosen from $C_2$–$C_4$ glycols, the ether derivatives of a $C_2$–$C_4$ glycol and mixtures thereof, and
at least one solvent for oil and water, containing an alcohol functional group. The composition is further free of surfactants.

Water in the vehicle according to the invention is preferably present in a quantity ranging from 1 to 10% by weight relative to the total weight of the vehicle.

The solvent containing an alcohol functional group may be especially a $C_2$–$C_8$ primary alcohol, a $C_5$–$C_7$ glycol or a mixture of both primary alcohol and of $C_5$–$C_7$ glycol.

Although free from surfactant and stabilizer, the vehicle according to the invention is in the form of a transparent or translucent fluid, exhibiting good stability. The absence of surfactant has the advantage of making the vehicle less irritating.

According to the invention, "amphiphilic oil" is intended to mean an oil which has affinities with water. It may involve in particular esters or ethers containing an oxygen atom which have affinities with water and which have an HLB (hydrophilic lipophilic balance) of 6 to 12, and preferably an HLB of approximately 10. Amphiphilic oils usable in the present invention preferably include laureth-2 benzoate, glycereth-7 benzoate, diethylene glycol dioctanoate/diisononanoate, polyoxypropylene-15 stearyl ether, 2-ethylhexyl malate, isopropyl adipate, the copolymer of PPG-7 and of succinic acid and neopentyl glycol dioctanoate.

The amphiphilic oil is preferably present in the vehicle of the invention in a quantity ranging from 10 to 55% by weight, and more preferably from 20 to 30% by weight, relative to the total weight of the vehicle.

Propylene glycol and butylene glycol are preferred $C_2$–$C_4$ glycols usable according to the invention. Furthermore, "ether derivative of a $C_2$–$C_4$ glycol" is intended to mean the glycols obtained by condensation of two $C_2$–$C_4$ glycols with formation of an ether bond, such as dipropylene glycol, and their derivatives such as the ethoxydiglycol (for example, sold under the name of TRANSCUTOL by Gattefosse).

Preferred $C_5$–$C_7$ glycols usable according to the invention include 1,2-pentanediol (for example, sold under the name HYDROLITE-5 by Dragoco).

A preferred primary alcohol usable in the vehicle of the invention is ethyl alcohol.

The vehicle according to the invention may contain from 10 to 20% by weight of one or more $C_2$–$C_4$ glycols and/or of one or more ether derivatives of a $C_2$–$C_4$ glycol and preferably from 15 to 18% by weight relative to the total weight of the vehicle.

Furthermore, the vehicle according to the invention may contain from 5 to 60% by weight, and preferably from 15 to 55% by weight, of one or more primary alcohols and/or of one or more $C_5$–$C_7$ glycols. The quantity of $C_5$–$C_7$ glycol advantageously changes from 5 to 10% by weight when the vehicle contains a primary alcohol.

The vehicle of the invention may advantageously be employed in a composition with topical action containing active substances that are sensitive to external factors such as light and heat and/or to water. These active substances surprisingly remain stable in the composition according to the invention.

In another embodiment, the present invention provides a composition containing an active substance with topical action, sensitive to external factors and/or to water, which contains a vehicle as defined above.

The active substances with topical action which are sensitive to external factors and/or to water and to which the invention can be applied may be especially enzymes and active substances containing at least one hydroxyl functional group.

Lipases and proteases may be mentioned, for example, as enzymes. Among proteases there may be mentioned, for example, that sold under the trade name SUBTILISINE SP 544 by the company Novo Nordisk and that sold under the trade name LYSOVEG by Laboratoires Sérobiologiques of Nancy.

As active substances containing at least one hydroxyl functional group there may be mentioned in particular the esterifiable vitamins such as retinol (vitamin A) and its derivatives, ascorbic acid (vitamin C) and its derivatives, and hydroxylated ketones such as dihydroxyacetone.

These active substances are advantageously present in the composition according to the invention in a quantity ranging from 0.5 to 10% by weight, and more particularly from 1 to 5% by weight, relative to the total weight of the composition.

For a topical application the composition according to the invention must contain a topically acceptable medium, that is to say compatible with the skin and/or the hair and/or the mucosae.

Depending on the active substance which it contains, the composition according to the invention can be employed for the cosmetic and/or dermatological treatment of the skin and/or of hair.

The composition according to the invention may in particular constitute cleansing, protective, treatment or care compositions for the face, for the neck, for the hands or for the body, artificial tanning products or products for the hair and especially for the care of the scalp, for example in the form of treating lotions.

In the particular case of ascorbic acid, the composition may be intended, for example, for the depigmentation of the skin or for the treatment of acne. The latter may also be treated with a composition containing retinol.

Accordingly, another embodiment of the invention is the use of the composition as defined above for the depigmentation of the skin, the active substance being ascorbic acid.

Another embodiment of the invention is the use of the composition as defined above for preparing a salve or a dermatological ointment intended for the therapeutic treatment of acne, the active substance being ascorbic acid and/or retinol.

When it contains dihydroxyacetone, the composition according to the invention may constitute a tanning composition.

Accordingly, another embodiment of the invention is the use of the composition as defined above for coloring the skin, the active substance being dihydroxyacetone.

The dihydroxyacetone is preferably employed in a quantity ranging from 1 to 8% by weight and, better, from 1 to 5% by weight relative to the total weight of the composition.

In addition, another embodiment of the invention is a tanning composition based on dihydroxyacetone, characterized in that it includes not more than 10% of water, at least one amphiphilic oil, at least one polyol or polyol derivative chosen from $C_2$–$C_4$ glycols, ether derivatives of a $C_2$–$C_4$ glycol and mixtures thereof, and at least one solvent for oil and water, containing an alcohol functional group.

In a known manner, the composition according to the invention may also contain adjuvants which are usual in the cosmetic or dermatological field, such as preservatives, antioxidants, perfumes, sunscreens, gelling agents, sequestrants, essential oils, colorants and hydrophilic or lipophilic active substances other than those indicated above.

Gelling agents which may be mentioned are, for example, polysaccharides such as hydroxypropyl celluloses.

Hydrophilic active substances which may be employed are, for example, proteins or protein hydrolysates and amino acids.

Lipophilic active substances which may be employed are, for example, tocopherol (vitamin E) and its derivatives, essential fatty acids, ceramides and essential oils.

The quantities of the various constituents of the composition according to the invention are those conventionally employed in the fields being considered.

EXAMPLES

Having generally described this invention, a further understanding can be obtained by reference to certain specific examples which are provided herein for purposes of illustration only and are not intended to be limiting unless otherwise specified.

The quantities shown are percentages by weight.

In all the examples the compositions are prepared in the following manner: if a gelling agent is present, it is dispersed when cold in the solvent containing an alcohol functional group (ethyl alcohol) with continuous stirring, and the various constituents are then added one after the other, after preliminary dilution of the active substances in water.

| Example 1: Tanning fluid | |
|---|---|
| Ethyl alcohol | 43.4% |
| Hydroxypropyl cellulose | 0.7% |
| Vitamin E | 0.5% |
| Butylene glycol | 10% |
| Dipropylene glycol | 5% |
| Laureth-2 benzoate (DERMOL 126 sold by Alzo) | 12.5% |
| Glycerth-7 benzoate (DERMOL G76 sold by Alzo) | 7.5% |
| Diethylene glycol dioctanoate/ diisononanoate (DERMOL 489 sold by Alzo) | 5% |
| Dihydroxyacetone | 5% |
| Perfume | 0.4% |
| Water | 10% |

The fluid obtained is in the form of a transparent liquid, stable with time, pleasant to apply. It permits uniform tanning of the face and of the body by daily application for at least one week.

A use test was performed on a panel of 40 women who applied the tanning fluid to the face for 10 days.

The users assessed the transparency of the fluid and indicated that it was easy to apply and particularly cool when applied to the skin. After the 10 days' use, they judged that the tanning had been obtained more quickly than with the usual compositions and that the coloring obtained was uniform. 73% of the users declared they were prepared to buy it.

| Example 2: Tanning fluid | |
|---|---|
| Ethyl alcohol | 33.2% |
| Hydroxypropyl cellulose | 0.7% |
| Vitamin E | 0.5% |
| Butylene glycol | 10% |
| Dipropylene glycol | 7.5% |
| Laureth-2 benzoate (DERMOL 126 sold by Alzo) | 10% |
| Diethylene glycol dioctanoate/ diisononanoate (DERMOL 489 sold by Alzo) | 8% |
| Polyoxypropylene-15 stearyl ether (ARLAMOL E sold by ICI) | 4.5% |
| 1,2-Pentanediol (HYDROLITE-5 sold by Dragoco) | 10% |
| Dihydroxyacetone | 5% |
| Perfume | 0.6% |
| Water | 10% |

The fluid obtained has the same characteristics as that in Example 1.

| Example 3: Tanning fluid | |
|---|---|
| Ethyl alcohol | 53.8% |
| Hydroxypropyl cellulose | 0.5% |
| Vitamin E | 0.5% |
| Butylene glycol | 15% |
| Diethylene glycol dioctanoate/ diisononanoate (DERMOL 489 sold by Alzo) | 20% |
| Dihydroxyacetone | 5% |
| Perfume | 0.2% |
| Water | 5% |

The fluid obtained has the same characteristics as that in Example 1.

| Example 4: Tanning fluid | |
|---|---|
| Ethyl alcohol | 53.8% |
| Hydroxypropyl cellulose | 0.5% |
| Butylene glycol | 15% |
| Diethylene glycol dioctanoate/ diisononanoate (DERMOL 489 sold by Alzo) | 15.5% |
| Polyoxypropylene-15 stearyl ether (ARLAMOL E sold by ICI) | 5% |
| Dihydroxyacetone | 5% |
| Perfume | 0.2% |
| Water | 5% |

The fluid obtained has the same characteristics as that in Example 1.

| Example 5: Tanning fluid | |
|---|---|
| Ethyl alcohol | 37.2% |
| Hydroxypropyl cellulose | 0.1% |
| Butylene glycol | 15% |
| Diethylene glycol dioctanoate/ diisononanoate (DERMOL 489 sold by Alzo) | 30% |
| Polyoxypropylene-15 stearyl ether (ARLAMOL E sold by ICI) | 5.5% |
| Dihydroxyacetone | 7% |
| Perfume | 0.2% |
| Water | 5% |

The fluid obtained has the same characteristics as that in Example 1.

Example 6: Tanning fluid

| | |
|---|---|
| Ethyl alcohol | 28.8% |
| Vitamin E | 0.5% |
| Butylene glycol | 15% |
| Diethylene glycol dioctanoate/ diisononanoate (DERMOL 489 sold by Alzo) | 50% |
| Dihydroxyacetone | 3% |
| Perfume | 0.2% |
| Water | 2.5% |

The fluid obtained has the same characteristics as that in Example 1.

Example 7: Tanning fluid

| | |
|---|---|
| Ethyl alcohol | 54.3% |
| Butylene glycol | 15% |
| Polyoxypropylene-15 stearyl ether (ARLAMOL E sold by ICI) | 20.5% |
| Dihydroxyacetone | 5% |
| Perfume | 0.2% |
| Water | 5% |

The fluid obtained has the same characteristics as that in Example 1.

Example 8: Tanning fluid

| | |
|---|---|
| Ethyl alcohol | 34.2% |
| Hydroxypropyl cellulose | 0.1% |
| Vitamin E | 0.5% |
| Butylene glycol | 10% |
| Dipropylene glycol | 7.5% |
| Laureth-2 benzoate (DERMOL 126 sold by Alzo) | 5% |
| Diethylene glycol dioctanoate/ diisononanoate (DERMOL 489 sold by Alzo) | 12.1% |
| Polyoxypropylene-15 stearyl ether (ARLAMOL E sold by ICI) | 5% |
| 2-Ethylhexyl malate | 5% |
| Ethoxydiglycol | 10% |
| Dihydroxyacetone | 5% |
| Perfume | 0.6% |
| Water | 5% |

The fluid obtained has the same characteristics as that in Example 1.

Example 9: Depigmenting fluid

| | |
|---|---|
| Ethyl alcohol | 33.5% |
| Hydroxypropyl cellulose | 0.7% |
| Vitamin E | 0.5% |
| Butylene glycol | 10% |
| Dipropylene glycol | 7.5% |
| Diethylene glycol dioctanoate/ diisononanoate (DERMOL 489 sold by Alzo) | 10% |
| Laureth-2 benzoate (DERMOL 126 sold by Alzo) | 10% |
| Polyoxypropylene-15 stearyl ether (ARLAMOL E sold by ICI) | 7.5% |
| 1,2-Pentanediol (HYDROLITE-5 sold by Dragoco) | 10% |
| Ascorbic acid | 5% |
| Perfume | 0.3% |
| Water | 5% |

The fluid obtained is in the form of a stable, transparent liquid which is pleasant to apply. Its regular application allows marks to be removed from the skin.

Example 10: Cleansing fluid

| | |
|---|---|
| Ethyl alcohol | 33.8% |
| Hydroxypropyl cellulose | 0.7% |
| Butylene glycol | 10% |
| Dipropylene glycol | 7.5% |
| Diethylene glycol dioctanoate/ diisononanoate (DERMOL 489 sold by Alzo) | 10% |
| Laureth-2 benzoate (DERMOL 126 sold by Alzo) | 10% |
| Polyoxypropylene-15 stearyl ether (ARLAMOL E sold by the company ICI) | 8% |
| 1,2-Pentanediol (HYDROLITE-5 sold by Dragoco) | 10% |
| Enzyme (SUBTILISINE SP 544 by Novo Nordisk) | 0.1% |
| Water | 9.9% |

A transparent fluid is obtained, intended for cleansing the skin of the face and of the body.

An analytical test was carried out to determine the stability of dihydroxyacetone after storage at 45C for a certain time, for two compositions according to the invention (Examples 11 and 12) and two comparative compositions (Counterexamples 1 and 2), the dihydroxyacetone content being initially 5% in all the compositions.

The compositions tested were the following:

Example 11: Tanning fluid according to the invention

| | |
|---|---|
| Ethyl alcohol | 59.3% |
| Vitamin E | 0.5% |
| Butylene glycol | 15% |
| Diethylene glycol dioctanoate/ diisononanoate (DERMOL 489 sold by Alzo) | 10% |
| Dihydroxyacetone | 5% |
| Perfume | 0.2% |
| Water | 10% |

Example 12: Tanning fluid according to the invention

| | |
|---|---|
| Ethyl alcohol | 54.3% |
| Vitamin E | 0.5% |
| Butylene glycol | 15% |
| Diethylene glycol dioctanoate/ diisononanoate (DERMOL 489 sold by Alzo) | 15% |
| Polyoxypropylene-15 stearyl ether (ARLAMOL E sold by ICI) | 5% |
| Dihydroxyacetone | 5% |
| Perfume | 0.2% |
| Water | 5% |

Comparative Example 1: Tanning gel

| | |
|---|---|
| Methyl vinyl ether/maleic anhydride copolymer crosslinked with 1,9-decadiene (STABILEZE 06 sold by ISP) | 0.5% |
| 2-Amino-2-methyl-1-propanol | 0.25% |
| Ethyl alcohol | 45% |
| Butylene glycol | 15% |
| Diethylene glycol dioctanoate/ diisononanoate (DERMOL 489 sold by |  |

-continued

| Comparative Example 1: Tanning gel | |
|---|---|
| Alzo) | |
| Hydrogenated castor oil PEG-60 (CREMOPHOR RH60 sold by BASF) | 0.5% |
| Dihydroxyacetone | 5% |
| Perfume | 0.2% |
| Water | 13.55% |

The gel of Comparative Example 1 is translucent and not very fluid. It differs from the compositions of the invention in a higher water content.

| Comparative Example 2: Tanning microemulsion | |
|---|---|
| Isohexadecane (ARLAMOL HD sold by the company ICI) | 44% |
| Dimethicone (DOW CORNING 200 FLUID sold by Dow Corning) | 18.8% |
| Mixture of PEG-8 OE and glyceryl laurate (surfactant) | 21.6% |
| Lauric Plurol (surfactant) | 5.4% |
| Dihydroxyacetone | 5% |
| Perfume | 0.2% |
| Water | 5% |

A transparent microemulsion is obtained which differs from the compositions of the invention in the fact that the oils employed are not amphiphilic and in the presence of surfactant.

The results of Examples 11 and 12 and of Comparative Examples 1 and 2 are shown in the following table:

| Number of days at 45° C. | Example 11 (invention) | Example 12 (invention) | Comparative Example 1 | Comparative Example 2 |
|---|---|---|---|---|
| 30 | 3.9 | 4.8 | 3.7 | 1.9 |
| 50 | 4.2 | 4.7 | 1.5 | 2.0 |

With the quantity of dihydroxyacetone at TO being 5%, these results clearly show that the compositions according to the invention maintain the activity of dihydroxyacetone for a longer time than their comparative products. From this it follows that the stability of dihydroxyacetone in the compositions according to the invention is markedly higher than that of the prior art.

Having now fully described the invention, it will be apparent to one of ordinary skill in the art that many changes and modifications can be made thereto without departing from the spirit or scope of the invention as set forth herein.

This application is based on French application 95-12446, filed Oct. 23, 1995. The full text of that priority is incorporated herein by reference.

What is claimed as new and desired to be secured by Letters Patent of the United States is:

1. A vehicle which comprises:
   not more than 10% by weight of water, based on the total weight of the vehicle,
   at least one amphiphilic oil,
   at least one polyol or polyol derivative selected from the group consisting of $C_2$–$C_4$ glycols, ether derivatives of a $C_2$–$C_4$ glycol and mixtures thereof, and
   at least one solvent for oil and water, containing an alcohol functional group;
   wherein said vehicle is surfactant free.

2. The vehicle according to claim 1, wherein the solvent is a $C_2$–$C_8$ primary alcohol, $C_5$–$C_7$ glycol or a mixture thereof.

3. The vehicle according to claim 1, which comprises from 1 to 10% by weight of water.

4. The vehicle according to claim 1, which is free of stabilizers.

5. The vehicle according to claim 1, wherein the amphiphilic oil is a ester or an ether containing an oxygen atom which has an affinity with water and which has an HLB of 6 to 12.

6. The vehicle according to claim 5, wherein the amphiphilic oil is selected from the group consisting of laureth-2 benzoate, glycereth-7 benzoate, diethylene glycol dioctanoate/diisononanoate, polyoxypropylene-15 stearyl ether, 2-ethylhexyl malate, isopropyl adipate, a copolymer of PPG-7 and of succinic acid, neopentyl glycol dioctanoate and mixtures thereof.

7. The vehicle according to claim 1, wherein the $C_2$–$C_4$ glycol is selected from the group consisting of propylene glycol, butylene glycol and mixtures thereof.

8. The vehicle according to claim 1, wherein the ether derivative of a $C_2$–$C_4$ glycol is selected from the group consisting of dipropylene glycol, ethoxydiglycol and mixtures thereof.

9. The vehicle according to claim 2, wherein the primary alcohol is ethanol.

10. The vehicle according to claim 2, wherein the $C_5$–$C_7$ glycol is 1,2-pentanediol.

11. The vehicle according to claim 1, wherein the amphiphilic oil is present in a quantity ranging from 10 to 55% by weight relative to the total weight of the vehicle.

12. The vehicle according to claim 1, wherein the polyol or polyol derivative is present in a quantity ranging from 10 to 20% by weight relative to the total weight of the vehicle.

13. The vehicle according to claim 1, wherein the solvent is present in a quantity ranging from 5 to 60% by weight relative to the total weight of the vehicle.

14. A composition comprising:
   (i) an active substance with topical action which is sensitive to external factors or to water and
   (ii) a vehicle which comprises
   not more than 10% by weight, of water based on the total weight of the vehicle,
   at least one amphiphilic oil, at least one polyol or polyol derivative selected from the group consisting of $C_2$–$C_4$ glycols, ether derivatives of a $C_2$–$C_4$ glycol and mixtures thereof, and
   at least one solvent for oil and water, containing an alcohol functional group;
   wherein said vehicle is surfactant free.

15. The composition according to claim 14, wherein the active substance with topical action is selected from the group consisting of enzymes and active substances containing at least one hydroxyl functional group.

16. The composition according to claim 15, wherein the active substance containing at least one hydroxyl functional group is selected from the group consisting of esterifiable vitamins, hydroxylated ketones and mixtures thereof.

17. The composition according to claim 16, wherein the active substance containing at least one hydroxyl functional group is chosen from the group including retinol, ascorbic acid, dihydroxyacetone and mixtures thereof.

18. The composition according to claim 14, wherein the active substance with topical action is present in a quantity ranging from 0.5 to 10% by weight relative to the total weight of the composition.

19. The composition according to claim 14, which is a cosmetic or dermatological composition.

20. The composition according to claim 14, which further comprises at least one lipophilic or hydrophilic adjuvant selected from the group consisting of preservatives, antioxidants, perfumes, sunscreens, gelling agents, sequestrants, essential oils and colorants.

21. A method for the depigmentation of the skin, comprising applying the composition of claim 14 to the skin, wherein the active substance is ascorbic acid.

22. A method for improving skin radiance, comprising applying the composition of claim 14 to the skin, wherein the active substance is ascorbic acid.

23. A method for treating acne, comprising applying the composition according to claim 14, wherein the active substance is ascorbic acid, or a mixture thereof.

24. A method for tanning skin, comprising applying the composition according to claim 14 to the skin, wherein the active substance is dihydroxyacetone.

25. A tanning composition comprising dihydroxyacetone as active agent and a vehicle comprising not more than 10% by weight of water, based on the total weight of the composition, at least one amphiphilic oil, at least one polyol or polyol derivative chosen from $C_2$–$C_4$ glycols, ether derivatives of a $C_2$–$C_4$ glycol and mixtures thereof, and at least one solvent for oil and water, containing an alcohol functional group.

26. The tanning composition according to claim 25, wherein the dihydroxyacetone is present in a quantity ranging from 1 to 8% by weight relative to the total weight of the composition.

* * * * *